United States Patent
Jones

(10) Patent No.: US 10,375,323 B2
(45) Date of Patent: Aug. 6, 2019

(54) IN-TIME REGISTRATION OF TEMPORALLY SEPARATED IMAGES ACQUIRED WITH IMAGE ACQUISITION SYSTEM HAVING THREE DIMENSIONAL SENSOR

(71) Applicant: Epitomyze Inc., Pound Ridge, NY (US)

(72) Inventor: Freddy Jones, Pound Ridge, NY (US)

(73) Assignee: Epitomyze Inc., Pound Ridge, NY (US)

( * ) Notice: Subject to any disclaimer, the term of this patent is extended or adjusted under 35 U.S.C. 154(b) by 0 days.

(21) Appl. No.: 15/830,539

(22) Filed: Dec. 4, 2017

(65) Prior Publication Data

US 2018/0220083 A1    Aug. 2, 2018

Related U.S. Application Data

(63) Continuation of application No. 15/076,367, filed on Mar. 21, 2016, now Pat. No. 9,866,767, which is a (Continued)

(51) Int. Cl.
*H04N 5/272* (2006.01)
*H04N 5/232* (2006.01)
*G06T 19/00* (2011.01)

(52) U.S. Cl.
CPC ......... *H04N 5/272* (2013.01); *H04N 5/23222* (2013.01); *H04N 5/23293* (2013.01); *G06T 19/006* (2013.01); *G06T 2207/10028* (2013.01)

(58) Field of Classification Search
CPC ........... H04N 5/23206; H04N 5/23216; H04N 5/23222; H04N 5/23293; H04N 5/2621;
(Continued)

(56) References Cited

U.S. PATENT DOCUMENTS

| 5,151,945 A | 9/1992 | Lee et al. |
| 7,806,824 B2 | 10/2010 | Ohtake |

(Continued)

FOREIGN PATENT DOCUMENTS

| EP | 1465133 | 10/2004 | |
| EP | 2323102 | * 5/2011 | ............... G06T 7/00 |

(Continued)

*Primary Examiner* — Twyler L Haskins
*Assistant Examiner* — Akshay Trehan
(74) *Attorney, Agent, or Firm* — Mattingly & Malur, PC

(57) ABSTRACT

Embodiments facilitate in-time registration of temporally separated image acquisition sessions to obtain highly comparable images without physical restraint of the camera and/or subject. For example, while displaying a live view being acquired of a subject in real time in a viewfinder window of an image acquisition system, a live position of the system can be measured, a real-time offset can be computed between the live position and a guide position (corresponding to a position from which a prior image of the subject was acquired at a prior acquisition time), and a guide can be overlaid on the viewfinder window to indicate a real-time positional offset between the live view and the prior image according to the real-time offset. A present image of the subject can be acquired when the guide indicates an in-time registration between the live view and the prior image.

12 Claims, 5 Drawing Sheets

Related U.S. Application Data continuation of application No. PCT/US2015/034048, filed on Jun. 3, 2015.

(60) Provisional application No. 62/007,347, filed on Jun. 3, 2014.

(58) Field of Classification Search
CPC ....... H04N 5/272; G06T 7/0016; G06T 7/003; G06T 7/0044; G06T 7/0065; G06T 2207/10016; G06T 2207/10024; G06T 2207/30004; G06T 2207/30088; G06T 1/0007; G06T 2207/10028; G06T 7/0012; G06T 7/0014; G06T 19/006; G06T 19/20; G06K 9/32; G06K 9/62; A61B 2090/364–368; A61B 5/7425
See application file for complete search history.

(56) References Cited

U.S. PATENT DOCUMENTS

| | | |
|---|---|---|
| 2002/0004404 A1 | 1/2002 | Squibbs |
| 2002/0044048 A1 | 4/2002 | Watanabe et al. |
| 2004/0189829 A1 | 9/2004 | Fukuda et al. |
| 2007/0010743 A1* | 1/2007 | Arai ................ A61B 8/13 600/443 |
| 2007/0030363 A1 | 2/2007 | Cheatle et al. |
| 2008/0126942 A1 | 5/2008 | Lee et al. |
| 2008/0247616 A1* | 10/2008 | Pescatore .......... A61B 90/36 382/128 |
| 2009/0213213 A1* | 8/2009 | Fright ............... A61B 5/1077 348/77 |
| 2009/0287271 A1 | 11/2009 | Blum et al. |
| 2010/0225773 A1 | 9/2010 | Lee |
| 2010/0304720 A1 | 12/2010 | Lucero et al. |
| 2011/0102630 A1 | 5/2011 | Rukes |
| 2011/0292221 A1 | 12/2011 | Gu et al. |
| 2012/0099012 A1 | 4/2012 | Ryu et al. |
| 2014/0022405 A1 | 1/2014 | Muehrke et al. |

FOREIGN PATENT DOCUMENTS

| | | | |
|---|---|---|---|
| KR | 1020040070152 | 8/2004 | |
| WO | 2011063034 | 5/2011 | |
| WO | 2012083349 | 6/2012 | |
| WO | WO 2012/083349 * | 6/2012 | ............. A61B 5/00 |

* cited by examiner

IN-TIME REGISTRATION OF TEMPORALLY SEPARATED IMAGES ACQUIRED WITH IMAGE ACQUISITION SYSTEM HAVING THREE DIMENSIONAL SENSOR

FIELD

Some embodiments relate to digital image acquisition, and, more particularly, to in-time registration of temporally separated image acquisition.

BACKGROUND

In many applications, it is desirable to take two or more, highly comparable photographs of an organic or otherwise changing or moving subject at two separate times. This can involve acquiring the photographs in a manner that ensures the subject is in substantially the same position in both photographs and that the relative position and orientation of the camera to the subject is substantially the same in both photographs. For example, suppose a plastic surgeon is performing neck lift surgery on the neck folds of a patient and desires, accordingly, to acquire a series of images of the patient before, during, and after surgery to record changes in skin color, elasticity (e.g., how the skin hangs), etc. From one image to another, these changes can be difficult to reliably compare optically if there is any appreciable change in the position or orientation of the camera, in the position or orientation of the patient's head, in the shape and/or size of the target region (e.g., if there is a reduction in swelling), etc. Accordingly, many traditional image registration approaches (e.g., mapping of features from one image to another) can be ineffective or sub-optimal.

While there are a number of conventional approaches to maintaining the positions and/or orientations (relative and/or absolute) of the subject and/or the acquisition device (e.g., the camera), most involve a physical structure that guides and/or holds the subject and/or the camera. For example, one system includes a bar that extends from a camera by a set distance, which, by holding the end of the bar against the subject, can ensure the camera is positioned a fairly consistent distance from the subject in multiple sessions. However, this approach does little to ensure that the camera is in the same overall position and orientation with respect to the subject from one acquisition session to another, and it does essentially nothing to ensure that the subject is in the same position from one acquisition session to another. Some other systems include boxes, platforms, and/or other structures to guide or even hold a subject in a particular position relative to a fixed camera. These approaches can hold both the camera and subject in a relatively stable relationship, but they generally involve specialized structures, which are often large, heavy, expensive, and difficult to configure.

BRIEF SUMMARY

Embodiments described herein include novel systems and methods for facilitating in-time registration in temporally separated image acquisition sessions to obtain highly comparable images without physical restraint of the camera and/or subject. For example, some embodiments can facilitate use of an augmented reality-capable image acquisition environment (e.g., a tablet computer with a camera) to assist a photographer in acquiring sufficiently similar images of a subject at two different times when the subject is organic or otherwise changing in position and/or shape, and the camera is not physically restrained (e.g., not fixed to a tripod or other structure).

According to one set of embodiments, a method is provided for in-time registration of images from temporally separated image acquisition sessions. The method includes: displaying, in a viewfinder window of an image acquisition system, a live view being acquired of a subject in real time; measuring a live position of the image acquisition system using a non-contact position sensor of the image acquisition system, such that the live position corresponds to a real-time position from which the live view of the subject is being acquired; computing a real-time offset between the live position and a guide position, the guide position corresponding to a position from which a prior image of the subject was acquired at a prior acquisition time; and overlaying a guide on the viewfinder window during the displaying, the guide indicating a real-time positional offset between the live view and the prior image according to the real-time offset between the live position and the guide position. Some such embodiments further include acquiring a present image of the subject when the guide indicates an in-time registration between the live view and the prior image.

BRIEF DESCRIPTION OF THE DRAWINGS

The present disclosure is described in conjunction with the appended figures.

In the appended figures, similar components and/or features can have the same reference label. Further, various components of the same type can be distinguished by following the reference label by a second label that distinguishes among the similar components. If only the first reference label is used in the specification, the description is applicable to any one of the similar components having the same first reference label irrespective of the second reference label.

DETAILED DESCRIPTION

In the following description, numerous specific details are set forth to provide a thorough understanding of the present invention. However, one having ordinary skill in the art should recognize that the invention can be practiced without these specific details. In some instances, circuits, structures, and techniques have not been shown in detail to avoid obscuring the present invention.

Figure 1:
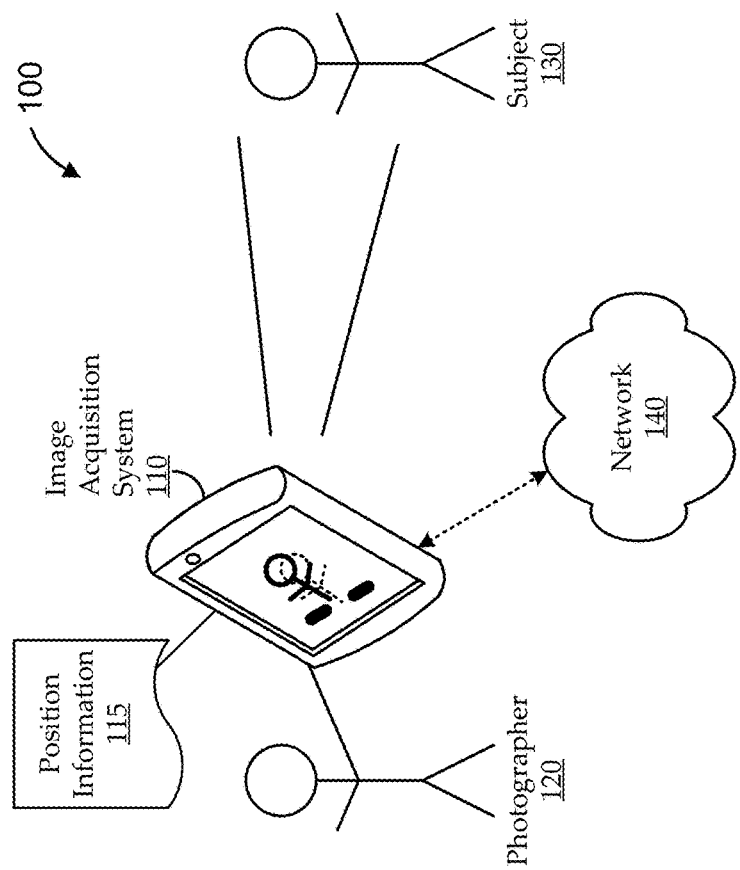
FIG. 1 shows an illustrative image acquisition environment in which a photographer can use a portable image acquisition system to acquire an image of a subject with in-time registration.

FIG. 1 shows an illustrative image acquisition environment 100 in which a photographer 120 can use a portable image acquisition system 110 to acquire an image of a subject 130 with in-time registration. As used herein, "in-time registration" is intended broadly to refer to techniques for registering present image acquisition to prior image acquisition while the present image acquisition is taking place. Such in-time registration can further involve post-processing for further registration and/or other types of functionality. Various embodiments described herein use fiducial-less techniques for in-time registration. For example, the registration can be performed without placing specialized markers on subjects or in the scene (e.g., as are commonly used in many photogrammetric, motion capture, and other environments).

While the illustrative environment shows a tablet or similar device, other implementations can involve any suitable image acquisition system 110. For example, the image acquisition system 110 can be a digital camera, a smart phone, a laptop computer, and/or any device or system that includes image acquisition, display, and other capabilities described herein. Further, while the illustrative environment shows a human subject 130, the subject 130 (image acquisition target) can be any suitable subject 130. For example, some functionality can facilitate temporally separated positioning of a human or animal subject 130, or a particular anatomical or other feature thereof (e.g., an arm, thigh, etc.). Other functionality can facilitate temporally separated imaging of a changing subject 130, such as a medical site (e.g., a lesion, an area of swelling, etc.), an organically changing structure (e.g., a glacier, microscopic object, cosmological event, etc.).

Some embodiments can be particularly useful in contexts in which the image acquisition system 110 and subject 130 are not physically restrained, or where their relative positions are not easily recreated from one image acquisition session to another. For example, unlike many conventional approaches, embodiments described herein can be used without additional structure for physically positioning and/or restraining movement of the image acquisition system 110 and subject 130. To that end, some embodiments exploit a combination of non-contact sensors and augmented reality display overlays to facilitate positioning and/or orienting of the image acquisition system 110 and/or subject 130.

As illustrated, some embodiments can be in communication with one or more networks 140. For example, data storage functions, computational functions, and/or other functions can be implemented over one or more public or private, wired or wireless, and/or any suitable networks 140. In various implementations, communications are secured to comply with one or more protocols (e.g., encryption schemas, communications protocols, etc.), statutes (e.g., data privacy statutes, etc), contractual obligations, etc.

Some embodiments include additional functionality. In some implementations, a series of images can, themselves, be used to further refine the acquisition position. For example, optical flow techniques, feature tracking, lighting changes, and/or other techniques can be applied in context of one or more images, which can indicate information about the position of the image acquisition system 110. In some implementations, imaging in non-visible frequency bands can be performed (which can further be temporally registered as described herein). For example, infrared imaging can provide information relating to inflammation in an anatomical region. In other implementations, three-dimensional (3D) imaging can be performed. Some such implementations use the 3D information to aid in registration. For example, 3D point clouds can be registered to each other, and/or 3D information can be used to automatically select an imaging angle from collected imaging data for use in registration to a previous image. Other such implementations can use the 3D information to derive volumetric, depth, and/or other 3D measurement information. For example, 3D information can be used to derive a volume of breast tissue before and after plastic surgery, a depth of a lesion, etc.

Figure 2:
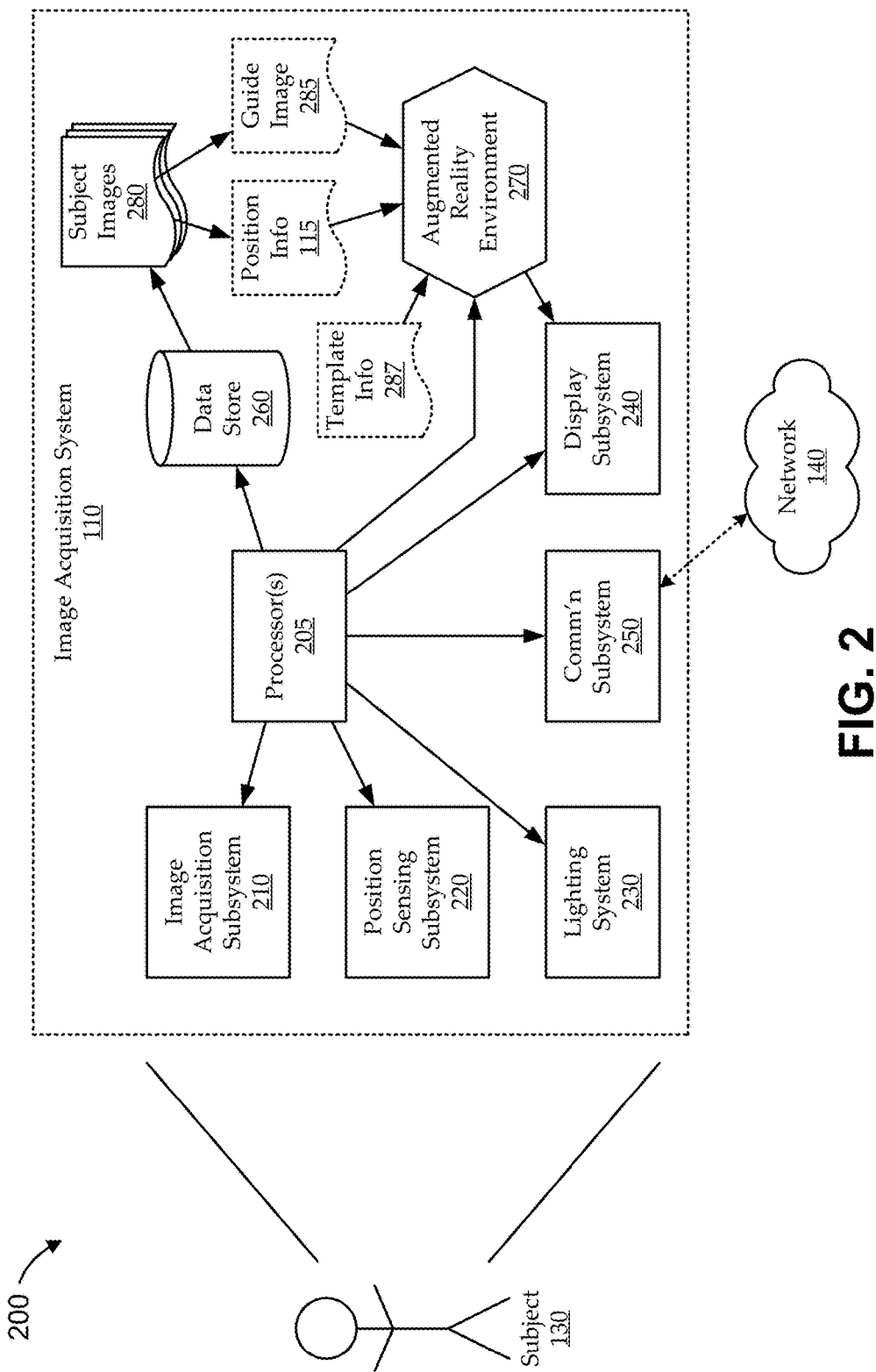
FIG. 2 shows an illustrative functional block diagram of an embodiment of an image acquisition environment, like the one shown in FIG. 1.

FIG. 2 shows an illustrative functional block diagram of an embodiment of an image acquisition environment 200, like the one shown in FIG. 1. As illustrated, the image acquisition environment 200 can include an image acquisition system 110 (e.g., like the one illustrated in FIG. 1), which can include an image acquisition subsystem 210, a position sensing subsystem 220, a lighting subsystem 230, a communications subsystem 250, a display subsystem 240, a data storage subsystem 260, and one or more processors 205. The one or more processors 205 can include instructions for directing operation of some or all of the subsystems to implement functionality described herein and they can include general purpose microprocessors, or any commercially available processor, controller, microcontroller, state machine, or the like. Further, the processor(s) can be implemented as a combination of computing devices.

The various functional subsystems can include hardware and/or software component(s) and/or module(s), including, but not limited to circuits, application specific integrated circuits (ASICs), general purpose processors, digital signal processors (DSPs), field programmable gate arrays (FPGAs), programmable logic devices (PLD), discrete gates, transistor logic devices, discrete hardware components, or combinations thereof. For example, steps of methods or algorithms, or other functionality described in connection with embodiments, can be embodied directly in hardware, in a software module executed by a processor, or in a combination of the two. A software module may reside in any form of tangible storage medium (e.g., in the data storage subsystem 260). Some examples of storage media that may be used include random access memory (RAM), read only memory (ROM), flash memory, EPROM memory, EEPROM memory, registers, a hard disk, a removable disk, a CD-ROM and so forth. A storage medium may be coupled to the one or more processors 205, such that the processor(s) 205 can read information from, and write information to, the storage medium. In the alternative, the storage medium may be integral to the processor(s) 205. A software module may be a single instruction, or many instructions, and may be distributed over several different code segments, among different programs, and across multiple storage media. Thus, a computer program product may perform operations presented herein. For example, such a computer program product may be a computer readable tangible medium having instructions tangibly stored (and/or encoded) thereon, the instructions being executable by the processor(s) 205 to perform the operations described herein. The computer program product may include packaging material. Software or instructions may also be transmitted over a transmission medium. For example, software may be transmitted from a website, server, or other remote source using a transmission medium such as a coaxial cable, fiber optic cable, twisted pair, digital subscriber line (DSL), or wireless technology such as infrared, radio, or microwave.

Embodiments of the image acquisition subsystem 210 can include cameras, sensors, and/or any components for acquiring two- and/or three-dimensional data of the subject in any suitable frequency band (subject images 280). According to some embodiments, the image acquisition system 210 can be used to acquire a first image of the subject 230 at a first acquisition time. For example, during a visit to a doctor's office, a nurse or other individual can acquire the first image of a patient subject. The image can include two-dimensional image data, three-dimensional (3D) image data (e.g., 3D point data, 3D mesh data, 3D polygon data, etc.), color data, etc. Some implementations capture data to generate a 3D model of the subject with surface texture (e.g., from captured images), which can enable the system to display previously captured data from multiple desired viewing positions. For example, the image acquisition subsystem 210 can capture a combination of 3D data and 2D data from which it can generate textured polygons or any other suitable type of 3D model of the subject. Depending on the completeness of the 3D model, the captured data can be used to generate images of the subject as if captured by multiple desired camera positions (e.g., a virtual camera can be positioned in any desired location and/or orientation, even if the image acquisition subsystem 210 were never physically in in that position and/or orientation during the acquisition session).

Some implementations of the image acquisition system 110 include additional functionality to aid in the acquisition of image data. For example, implementations can include a lighting subsystem 230 that operates to light the subject during image acquisition. For example, the lighting subsystem 230 can include full spectrum, multi-spectral, hyperspectral, and/or any other suitable type of lighting. The lighting can be integral to, coupled with, or otherwise in communication with the image acquisition subsystem 210. In some implementations, the display subsystem 240 can also aid in acquiring images by operating as a virtual viewfinder.

In some embodiments, when the first image is acquired at the first acquisition time, the image acquisition system can record an acquisition position of the acquisition device using a position sensing subsystem 220 having one or more position sensors. For example, the image acquisition system 110 can include a tablet computer or other device that includes (e.g., integrated therein) or is in communication with (e.g., has coupled therewith) a range finder, an attitude sensor, an accelerometer, a gravity sensor, an altimeter, a global positioning satellite sensor, a radiofrequency sensor, a theodolite sensor, a metrology sensor, a 3D scanner sensor, and/or any other suitable position sensors. Some embodiments utilize only non-contact types of sensors. The recorded position can include any useful position information, such as distance from the subject 130 and/or from any other contextual object (e.g., a fixed-location object in the scene), height from the floor (e.g., or table, etc.), absolute or relative 3D position (e.g., X, Y, Z location), pitch, roll, yaw, etc.

The first image and/or the recorded acquisition position information can be stored in the data storage subsystem 260. The data storage subsystem 260 can include any useful storage, such as solid state storage integrated into and/or in communication with the image acquisition subsystem 210. For example, some or all of the data storage subsystem 260 can be "on-board" (i.e., integrated into the device) or networked (i.e., available over a network 140 via the communications subsystem 250 as a data server, network storage, cloud storage, etc.).

At some subsequent time (e.g., in a later doctor's visit, or otherwise in a subsequent image acquisition session), it is desired to acquire another image of the subject 130 that is substantially comparable to the first. For example, it can be desirable for the two images to be similar enough to support a particular diagnostic (e.g., medical) function, to discern a certain type and/or amount of change over time, or for any other desired purpose. Embodiments facilitate acquisition of a substantially comparable subsequent image by providing a live comparison between data from the first acquisition session and present data of the second acquisition session via an augmented environment of the image acquisition system 110.

In some embodiments, the display subsystem 240 of the image acquisition system 110 is used to display a virtual viewfinder that indicates what image data is presently in the view of the image acquisition subsystem 210. The display subsystem 240 can further support an augmented reality environment 270. The augmented reality environment 270 of the image acquisition system 110 can be used to overlay, on the viewfinder, various types of guide information generated from the first image acquisition session to aid in registration during the second image acquisition session. As illustrated, the guide information can include position information 115 (e.g., including present position information, previously recorded position information, and/or comparison information, such as indications of difference between the previously recorded and the present location information) and/or one or more guide images 285. For example, while the photographer is acquiring the second image, he may look at the virtual viewfinder on the display to see a "live" view of the subject 130. At the same time, the guide information can be overlaid on the live view using the augmented reality environment 270, so that the photographer can see how the live view of the subject 130 compares with the previously acquired view of the subject 130. The photographer can use that feedback to adjust the position (e.g., distance, height, orientation, zoom level, etc.) of the image acquisition system and/or to adjust the position of the subject (e.g., or to instruct the subject to adjust appropriately).

Any suitable guide information can be used. In some embodiments, the augmented reality environment 270 of the image acquisition system 110 is used to overlay, on the viewfinder, a guide image 285 generated from the first image (i.e., any image of the subject 130 previously acquired for the purpose of temporally separated registration). The guide image 285 can include two- and/or three-dimensional information and can be generated in any manner suitable to provide dynamic visual guidance for assisting the photographer in registering the subsequent image acquisition. In one implementation, the guide image 285 includes a 3D mesh generated from the first image. For example, the 3D mesh can be implemented as a 3D point cloud, a 3D wireframe, a set of 3D polygons, etc. In another implementation, the guide image 285 includes a semi-transparent version of the first image. For example, the first image is translucently overlaid on the viewfinder and may or may not have an adjustable transparency level (e.g., adjustable using one or more graphical user interface (GUI) controls). In still another implementation, the guide image 285 includes a silhouette or outline generated from the first image. For example, the augmented reality environment 270 can be used to make the silhouette or outline appear as a translucent overlay, as if it is behind the subject 130, etc. In yet another implementation, the guide image 285 includes a set of key feature points generated from the first image. Key feature points can be automatically and/or manually created and associated with relevant features of the image. For example, if the image is of a person's face, it may be helpful to provide key feature points at the tip of the nose, the bottom of the ear lobe, etc. Key feature points, outlines, 3D meshes, and/or other information can also be used in conjunction with other image data (e.g., to further augment the registration experience of the user). For example, key feature points can be overlaid on a semi-transparent two- or three-dimensional image to form the guide image 285.

In some embodiments, the guide information can indicate recorded position information 115 from the first acquisition session. For example, the augmented reality environment 270 of the image acquisition system 110 can be used to overlay, on the viewfinder, a present position indication in relation to recorded position information 115. In one implementation, the position indication includes a graphical readout similar to that of a compass, artificial horizon indicator, heading indicator, bubble level, etc. For example, the recorded position information 115 (i.e., the position the image acquisition subsystem was in when the first image was acquired) is set as a "center" or "level" position of a digital level indicator, or as a "center" or "north" position of a compass, or other suitable position in a respective readout. During the second acquisition session, the photographer can use dynamic feedback via the position indication to align the present position to the recorded position. In other implementations, the position information 115 can include any useful visual, audible, and/or other feedback to assist with positioning the image acquisition subsystem and/or the subject. For example, various implementations include textual data (e.g., an alphanumeric readout of present, recorded, and/or relative position information), graphical data (e.g., meters, graphs, colors, icons, pop-ups, etc. to indicate present, recorded, and/or relative position information), audible data (e.g., audio indicators, changes in pitch or other sounds, "spoken" instructions, etc. indicating present, recorded, and/or relative position information), etc. As described above, the position information 115 can be acquired and/or derived from functionality of one or more position sensors of the position sensing subsystem 220.

In other embodiments, the guide information can indicate acquisition template information 287. Such template information 287 can be provided during the first and/or second (and/or any subsequent) acquisition session, and can, for example, be selectively displayed. In some such embodiments, an acquisition template is derived from predefined specifications relating to how the acquired image data will be used. For example, in some clinical environments, it is desirable to capture certain images of certain sizes in certain orders, or the like, and the acquisition template information 287 can instruct, guide, drive, or force such image capturing. For the sake of illustration, suppose a plastic surgeon is acquiring images in preparation for a neck lift surgery, and it is desirable for the patient to hold her head in a very particular position. Rather than using physical constraints or approximate positioning, the template information 287 can include visual guides overlaid on the viewfinder in the augmented reality environment 270 to help the photographer (e.g., a nurse or technician) in orienting and locating the patient's head (e.g., the viewfinder can include crosshairs or other visual locators for proper positioning of the chin, etc.). Any other suitable template information 287 can be provided.

The guide information can be used to provide the photographer with dynamic feedback during acquisition of the second image to facilitate registration of the second image to the first image. In some implementations, the guide image 285 is passively overlaid on the viewfinder. In other implementations, the guide image 285 includes active dynamic feedback functionality. For example, as the live scene in the viewfinder becomes more correlated with the guide image 285 (or the underlying first image data from which the guide image 285 is derived), the guide image 285 can change color, the outline can become more or less pronounced, key feature points can become more or less visible (or can appear or disappear, become more or less numerous, etc.). Similar techniques can be used with the position indicators. For example, the position indicator can indicate a level of present correlation between the recorded and present positions, indicate which direction and/or type of movement or other change would improve the correlation, and/or provide any other suitable registration information in any suitable manner, for example, by change its look and/or feel, providing graphical or audible feedback, etc.

In some embodiments, feedback relating to the guide information can be derived from image processing. For example, the live image data and the guide image data can be correlated at the pixel level (or by groups of pixels, etc.) to determine present similarity between the images, and various image processing techniques can be used to help determine whether a particular direction or type of movement of the image acquisition subsystem would improve the correlation. In other embodiments, feedback relating to the guide information can be derived from position sensor data processing. For example, correlations can be determined between present position sensor data and recorded position sensor data. In some implementations, data from multiple position sensors is combined to achieve a substantially correlatable effect. For example, some applications may require that the camera is in substantially the same position, orientation, zoom level, etc. to achieve a desired level of registration between images; while other applications may find sufficient registration when the earlier and later camera positions are different, but achieve a substantially similar image (e.g., the camera is slightly higher and closer, but slightly zoomed out and tilted down, thereby achieving a substantially similar view of the subject). Some embodiments use various image processing techniques to refine acquisition position, registration, etc. For example, the series of images themselves can be used to further refine acquisition position by use of optical flow techniques, feature tracking, lighting changes in the image itself (which may indicate information about the position of the image acquisition device), etc.

Some implementations support partial or contextual registration. For example, suppose it is desired to record changes in appearance of a skin lesion on a patient's arm over time. Because the lesion is changing, it may not be desirable or useful to register the lesion to itself at different acquisition sessions. Instead, it may be preferable to register the patient's arm in one session to the arm in a second session, ignoring changes in the lesion for registration purposes. Various implementations permit selecting of particular regions of the guide image, live image, etc. for use in registration; selecting of certain regions of the first image in generating the guide image; masking off of certain regions during registration; etc. For example, the dynamic feedback may indicate sufficient correlation between only the desired regions of the images, even if other (e.g., ignored, unselected, masked-off, etc.) regions have appreciably changed between sessions.

In some embodiments, sufficient registrability can account for image processing functionality. For example, even though two images are acquired from different positions, some or all of one or both images can be used to register the other or others by mapping, skewing, recoloring, and/or otherwise transforming image data (e.g., using heuristics, image processing algorithms, etc.). Various applications may be more or less amenable to such manipulation and mapping of the image data. In some such embodiments, some or all of the raw acquisition data (i.e., non-transformed data) is maintained for later use, if desired.

For example, in some implementations, 3D information is gathered by acquiring point, polygon, texture-mapping, and/or other information from around the subject 130. In some instances, the acquired 3D information can be augmented with interpolated and/or extrapolated information. The acquired 3D information can be used to manufacture a 2D image by positioning a virtual camera in a desired location. In some instances, the manufacture 2D image can be virtually acquired from a particular camera position and/or orientation, even though no physical camera was ever in that particular position or orientation. Such a technique can be used to manufacture a desired first image (e.g., to manufacture a desired guide image 285 for registering the second image acquisition), to manufacture a second image (e.g., to dynamically fit the second image acquisition to one or more first images), to manufacture first and second images (e.g., to facilitate post-acquisition image generation and registration), etc.

Having positioned the image acquisition subsystem 210 and the subject 130 as appropriate to substantially register the second image acquisition to the first, embodiments can use the image acquisition subsystem 210 to acquire the second image of the subject. In some implementations, the photographer can selectively acquire one or more images (e.g., by interacting with a "capture" button or the like) when the photographer determines that the second image is substantially registered to the first image according to at least one of the guide image 285 or the position information 115 (e.g., or template information 287, or any other guide information). In other implementations, the image acquisition subsystem 210 can automatically acquire one or more images when the second image is determined to be registered to the first image according to the guide information (e.g., at least one of the guide image or the position indicator) within some predetermined threshold. For example, when the live capture data is sufficiently registrable to the first image, the image acquisition subsystem 210 can automatically capture the image without waiting for interaction from the photographer. In yet another implementation, the image acquisition subsystem 210 can prevent the photographer from acquiring images (e.g., disabling a "capture" button or the like) until the second image is substantially registrable to the first image according to guide information (e.g., at least one of the guide image or the position indicator). Such an implementation can include feedback to the photographer indicating when an image can be acquired. Some embodiments provide substantially real-time feedback to the photographer. For example, in manual acquisition embodiments, the image acquisition system 210 can indicate a goodness of fit of the second image after acquisition as a function of its correlation to the first image, its lighting quality, etc. in any suitable manner (e.g., by showing the images side-by-side, by providing an audible indication of a suitable or not suitable image, etc.).

Other embodiments can include additional functionality. As described above, some embodiments acquire 3D data as part of the first and/or second image acquisition. The 3D data can be used in a number of ways. Some implementations use the 3D data for 3D registration. For example, some or all of the techniques described above can aid a photographer in registering second image acquisition to first image acquisition in three dimensions (e.g., to sufficiently correlate six degrees of freedom of the image acquisition subsystem (X, Y, Z, pitch, roll, yaw), positioning of the subject, etc.). Some embodiments use the 3D information for image generation and registration, as described above.

Other implementations use the 3D data to provide volumetric functionality. For example, a volume can be calculated from the acquired 3D image data. The volume can be a single volume for an entire defined region of the image, a volume distribution over a region of the image, etc. The recorded volume from the first image acquisition session can be compared with volume information from the second image acquisition session and/or with pre-stored volume information. For the sake of illustration, long-term aesthetics of breast augmentation or reduction surgery can depend on relative breast volumes and/or volume distributions, and differences in volume may be less discernible (and/or more relevant) than aesthetic differences from one or more viewpoints. As another illustration, changes in both the size and depth of a wound can be used to determine healing progress or various issues with the wound. Accordingly, some embodiments can be used to record and/or derive both size and depth (e.g., using surface volumetric measurement, non-visible electromagnetic spectra, etc.) to aid in such determinations.

The above techniques can be used in multiple environments to gather multiple types of information. For example, environmental changes can be seen over time in glaciers, foliage, etc., such that it may be desirable to acquire imagery from a scene from a comparable camera (and/or sensor) position at different acquisition times, without having to keep a tripod, camera, and/or other physical guides in place. As another illustration, the life of a certain product may be a function of an amount of bubbling seen in a surface coating, and the volume of bubbling may be more relevant than the location or size of any individual bubble. Further, while embodiments are primarily described above with reference to acquisition of visual image data, other frequency bands and/or other sensors can be used to acquire additional information. For example, some embodiments can perform infrared imaging of a site for measuring and/or detecting inflammation and/or for other diagnostic purposes. Embodiments can also be used to enable certain types of diagnostic functions not achievable using other types of image registration techniques. For example, suppose it is desirable to image moles on a portion of a patient's leg to monitor changes in the moles over time, but the portion of the leg has a relatively constant cross-section, making it difficult to map two images of the portion of leg taken at two different times to each other. Techniques described herein can register the two acquisition sessions in a manner that enables precise mapping of changes in the shapes, sizes, volumes, etc. of each mole. Some implementations further permit acquiring volume information in multiple sessions or even collecting volume information from multiple sites (e.g., both breasts) during a single session and/or image, and comparing those volume measurements. Some or all of the techniques described above can be used to provide dynamic registration information via the augmented reality environment, to provide dynamic registration feedback, etc.

Figure 3:
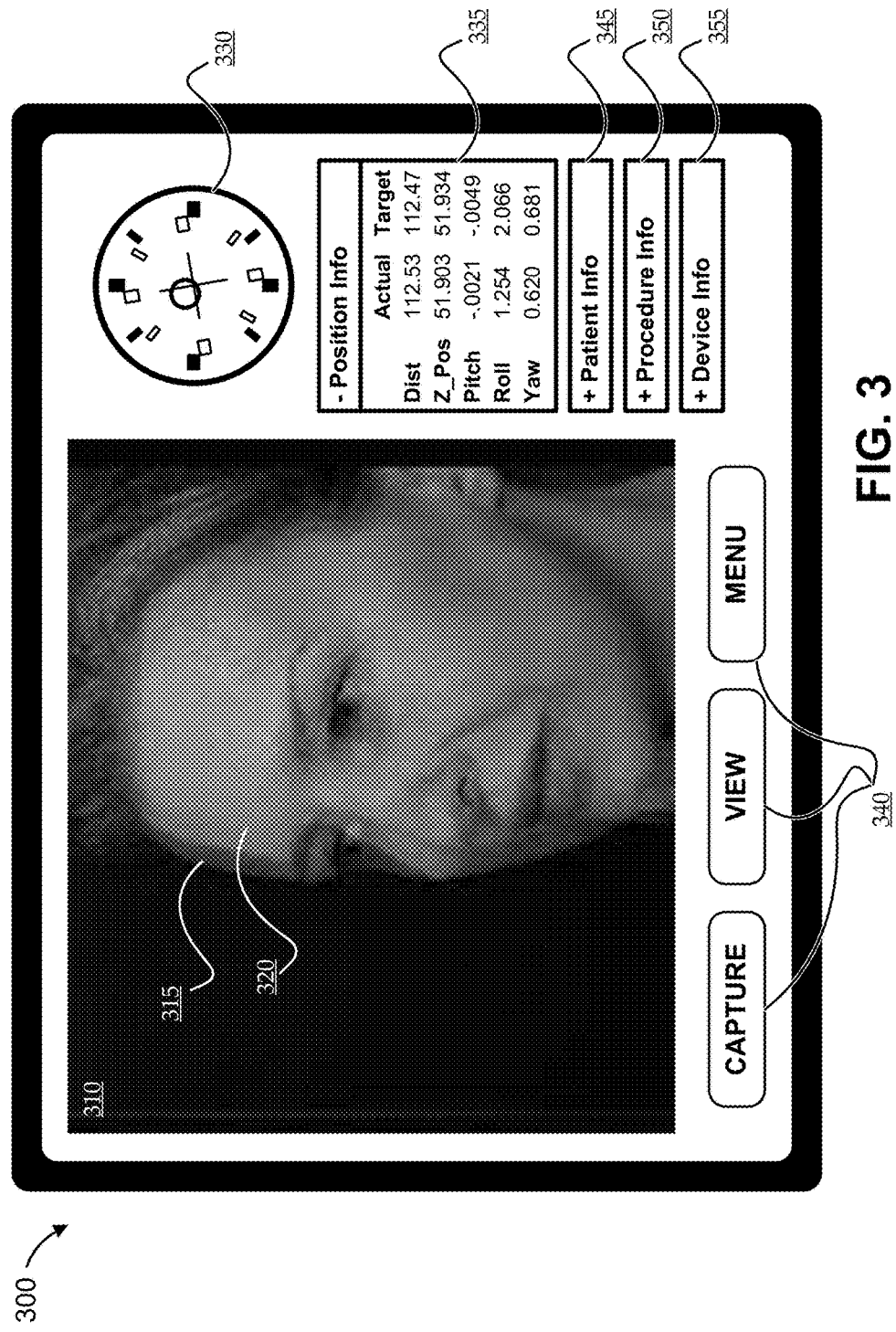
FIG. 3 shows one implementation of a user interface for providing certain augmented reality environment and guide information functionality described herein.

For the sake of illustration, FIG. 3 shows one implementation of a user interface 300 for providing certain augmented reality environment and guide information functionality described herein. The user interface 300 can be provided on a tablet computer, a camera, or any other dedicated or general purpose device having suitable capabilities. As shown, the user interface 300 can include a viewfinder window 310 that shows a live view 320 of the subject overlaid with guide image 315 data from an earlier acquisition session. The illustrated guide image 315 can be a 2D or 3D image. Alternatively (or additionally) the guide image can include any suitable guide information. To the right of the viewfinder window, various types of position information are shown. For example, a compass/level indicator 330 is shown having its center determined as a function of first image data, and a "position info" window 335 is shown having alphanumeric representations of recorded and present position information.

It is noted that, while some descriptions above refer to the guide information as overlaid on the viewfinder via the augmented reality environment, such descriptions are not intended to limit the location of such information to a particular region of the user interface 300. For example, the positions of the location information illustrated in FIG. 3 can be considered as overlaid on the viewfinder. Some implementations of the use interface include additional controls 340, such as a "capture" control (e.g., for manually acquiring an image), a "view" control (e.g., for changing parameters of the view, lighting controls, zoom, etc.), and a "menu" control (e.g., for providing access to one or more menus). Some implementations of the use interface also include additional information, such as a "patient info" window 345 (e.g., for providing or recording any relevant information about the patient or subject), a "procedure info" window 350 (e.g., for providing or recording information about the procedure, etc.), a "device info" window 355 (e.g., for providing or recording information about the image acquisition system or its particular components and/or components coupled or in communication therewith), etc. Various implementations permit any such interface elements (e.g., windows, menus, controls, etc.) to be selectively enabled/disabled, repositioned, reconfigured, etc.

Figure 4:
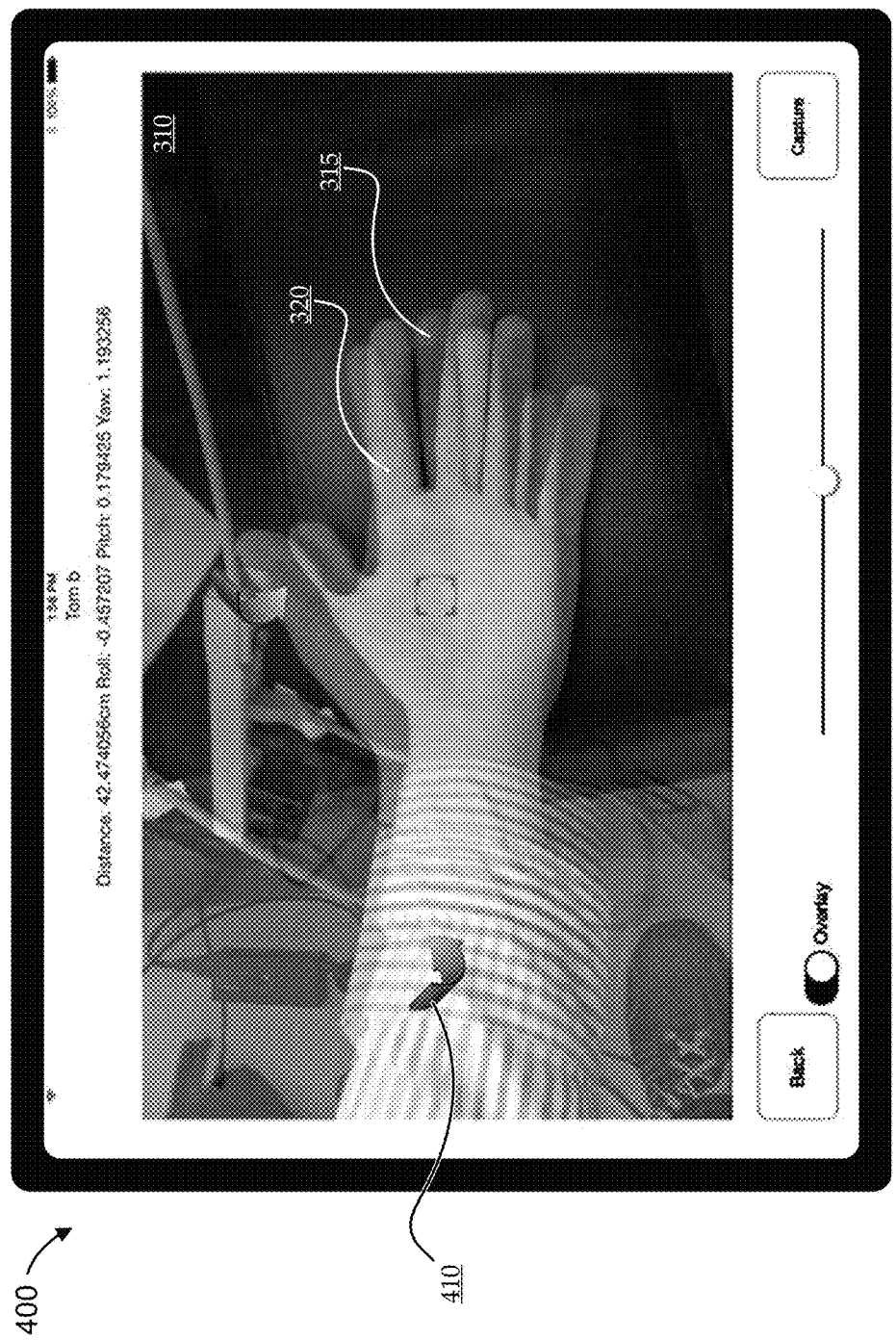
FIG. 4 shows another implementation of a user interface for providing certain augmented reality environment and guide information functionality described herein.

FIG. 4 shows another implementation of a user interface 400 for providing certain augmented reality environment and guide information functionality described herein. The user interface 400 is illustrated as a tablet display implementation, and shows image acquisition of a hand (with a live image 320 and a guide image 310). Various guide features and other interface elements are shown. For example, an arrow 410 is overlaid on the viewfinder window 310 to direct the photographer to tilt the device (and its camera) in the indicated direction. Also, the top of the display shows alphanumeric representations of position information. Below the viewfinder window 310, various interface elements are shown, including back and capture buttons (e.g., for moving back in a menu hierarchy and capturing an image, respectively), an overlay selector switch (e.g., for toggling the overlay guide image on and off), and an overlay slider (e.g., for changing the transparency level of the overlay guide image). The particular types and arrangement of guide information and interface elements shown in FIG. 4 is intended only to illustrate certain functionality and is not intended to be limiting.

Figure 5:
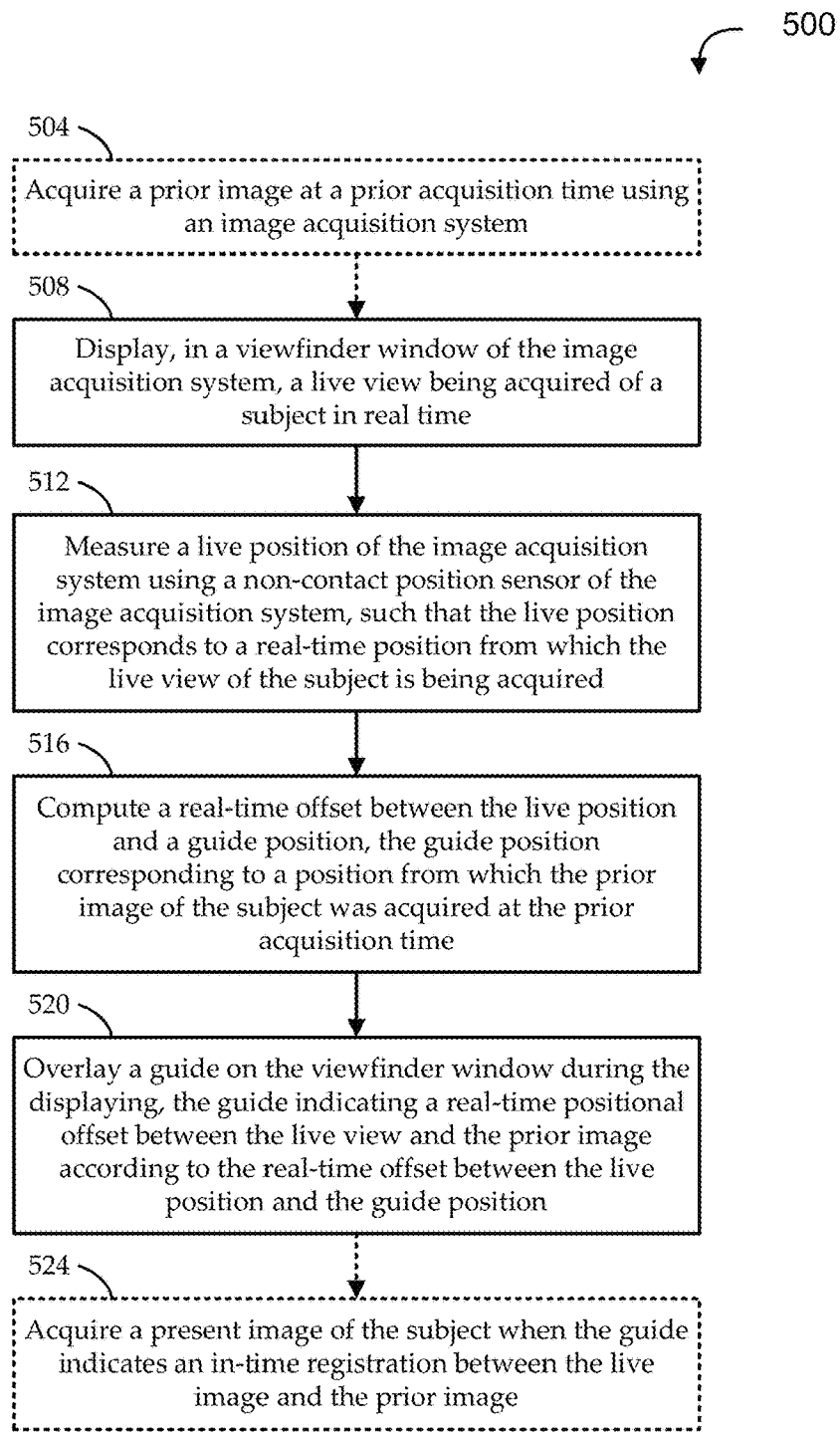
FIG. 5 shows a flow diagram of an illustrative method for in-time registration of images from temporally separated image acquisition sessions, according to various embodiments.

FIG. 5 shows a flow diagram of an illustrative method 500 for in-time registration of images from temporally separated image acquisition sessions, according to various embodiments. Some embodiments of the method 500 begin at stage 504 by acquiring a prior image at a prior acquisition time using an image acquisition system. For example, as described above, the prior image can be acquired to include any suitable two-dimensional and/or three-dimensional data of a subject, and can also include positional information of the image acquisition system at the time of acquisition. For example, the positional information can indicate the location, orientation, and/or other attributes of the camera and/or sensors used to acquire the prior image of the subject, and the data can be in any suitable reference framework (e.g., absolute position, relative to a room or other landmark, relative to the subject, etc.). The subject can be any suitable subject, such as some or all of a human patient.

At stage 508 (at some subsequent time), the method 500 can continue by displaying, in a viewfinder window of an image acquisition system, a live view being acquired of a subject in real time. The image acquisition system used in stage 508 can be the same or different from the one used in stage 504. For example, the image acquisition system can be implemented as one or more computational devices that include a camera and a display, such that the display can show (e.g., via a virtual viewfinder) what is presently being "seen" by the camera. In some implementations, the image acquisition system is a single device, such as a tablet computer that may have its various functions integrated into the device and/or coupled with the device (e.g., via one or more wired and/or wireless ports).

At stage 512, a live position of the image acquisition system can be measured using one or more non-contact position sensors of the image acquisition system, such that the live position corresponds to a real-time position from which the live view of the subject is being acquired. As described above, the non-contact sensors can include one or more of a range finder, an attitude sensor, an accelerometer, a gravity sensor, an altimeter, a global positioning satellite sensor, a radiofrequency sensor, a theodolite sensor, a metrology sensor, a three-dimensional scanner sensor, and/or any other suitable sensor. Again, the position information can include any suitable information in any suitable reference framework. At stage 516, a real-time offset can be computed between the live position and a guide position, the guide position corresponding to a position from which the prior image of the subject was acquired at the prior acquisition time (e.g., in stage 504).

At stage 520, embodiments can overlay a guide on the viewfinder window during the displaying, the guide indicating a real-time positional offset between the live view and the prior image according to the real-time offset between the live position and the guide position. As described above, the guide can include any suitable information for indicating the real-time positional offset. In some implementations, overlaying the guide can involve overlaying the prior image as a guide image on the viewfinder window. For example, the guide image can include a three-dimensional mesh generated from the prior image, a semi-transparent version of the prior image, a silhouette generated from the prior image, a plurality of key feature points generated from the prior image, etc. In other implementations, overlaying the guide can involve generating the guide as a directional indicator that indicates a direction of the real-time offset, such that the direction indicator shows a direction in which to move the image acquisition system to increase correspondence between the live position and the guide position, and overlaying the directional indicator on the viewfinder window. For example, the directional indicator can include an arrow, a compass, and/or any suitable indicator for telling an operator how to move the image acquisition system (e.g., the camera) and/or the subject. In certain implementations, overlaying the guide can involve generating a graphical template according to a predefined set of image acquisition criteria used to acquire the prior image, and overlaying the graphical template on the viewfinder window. For example, a medical diagnostic procedure or other scenario can be associated with a template that shows, virtually, how a camera and/or patient should be situated, etc. The template can, in some instances, be implemented as augmented reality guides for positioning real-world objects to facilitate image acquisition. In some embodiments, the guide further includes dynamic feedback indicating a real-time level of correspondence between the live position and the guide position. For example, visual feedback (e.g., darkening, color changing, changing font or typeface, etc.), audio feedback (e.g., beeping frequency, etc.), haptic feedback (e.g., vibration, etc.), and/or other types of feedback can dynamically indicate a level of correspondence. As one example, the guide image can be a semi-transparent version of the prior image rendered with a hue that progresses from red to green as the live position gets closer to the guide position.

In some embodiments, at stage 524, the method 500 can acquire a present image of the subject when the guide indicates an in-time registration between the live view and the prior image. In some implementations, the present image can be acquired in response to receiving a command from a human user to acquire the present image of the subject when the graphical guide indicates an in-time registration between the live image and the prior image. In other implementations, the present image can be acquired automatically upon detecting the in-time registration between the live view and the prior image within a predefined threshold. For example, when the real-time positions of the camera and the subject are detected to sufficiently match the conditions of the prior acquisition time, the present image can be automatically triggered. Some implementations can prevent acquisition of the present image until there is sufficient in-time registration between the live view and the prior image (e.g., within a predefined threshold).

In some embodiments, the prior image includes prior three-dimensional data acquired at the prior acquisition time (e.g., using a three-dimensional scanner or camera), and the acquiring of the present image involves acquiring present three-dimensional data and deriving a present three-dimensional measurement of the subject, such that a three-dimensional change is computable between the present three-dimensional measurement and a prior three-dimensional measurement derived from the prior three-dimensional data. In some such embodiments, the three-dimensional measurements are volumetric measurements, such that a volumetric change is computable between a present volumetric measurement and a prior volumetric measurement derived from the prior three-dimensional data. For example, images can be acquired at different stages (e.g., before and after) of a breast augmentation or reduction surgery, and changes in breast volume can be recorded over time. In other such embodiments, the three-dimensional measurements are depth measurements of the subject, such that a depth change is computable between a present depth measurement and a prior depth measurement derived from the prior three-dimensional data.

The methods disclosed herein include one or more actions for achieving the described method. The method and/or actions can be interchanged with one another without departing from the scope of the claims. In other words, unless a specific order of actions is specified, the order and/or use of specific actions can be modified without departing from the scope of the claims.

The functions described can be implemented in hardware, software, firmware, or any combination thereof. If implemented in software, the functions can be stored as one or more instructions on a tangible computer-readable medium. A storage medium can be any available tangible medium that can be accessed by a computer. By way of example, and not limitation, such computer-readable media can include RAM, ROM, EEPROM, CD-ROM, or other optical disk storage, magnetic disk storage, or other magnetic storage devices, or any other tangible medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

A computer program product can perform certain operations presented herein. For example, such a computer program product can be a computer readable tangible medium having instructions tangibly stored (and/or encoded) thereon, the instructions being executable by one or more processors to perform the operations described herein. The computer program product can include packaging material. Software or instructions can also be transmitted over a transmission medium. For example, software can be transmitted from a website, server, or other remote source using a transmission medium such as a coaxial cable, fiber optic cable, twisted pair, digital subscriber line (DSL), or wireless technology such as infrared, radio, or microwave.

Further, modules and/or other appropriate means for performing the methods and techniques described herein can be downloaded and/or otherwise obtained by suitable terminals and/or coupled to servers, or the like, to facilitate the transfer of means for performing the methods described herein. Alternatively, various methods described herein can be provided via storage means (e.g., RAM, ROM, a physical storage medium such as a CD or floppy disk, etc.), such that a user terminal and/or base station can obtain the various methods upon coupling or providing the storage means to the device. Moreover, any other suitable technique for providing the methods and techniques described herein to a device can be utilized. Features implementing functions can also be physically located at various positions, including being distributed such that portions of functions are implemented at different physical locations.

In describing the present invention, the following terminology will be used: The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" means quantities, dimensions, sizes, formulations, parameters, shapes and other characteristics need not be exact, but can be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations including, for example, tolerances, measurement error, measurement accuracy limitations and other factors known to those of skill in the art, can occur in amounts that do not preclude the effect the characteristic was intended to provide. Numerical data can be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3 and 4 and sub-ranges such as 1-3, 2-4 and 3-5, etc. This same principle applies to ranges reciting only one numerical value (e.g., "greater than about 1") and should apply regardless of the breadth of the range or the characteristics being described. A plurality of items can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items can be used alone or in combination with other listed items. The term "alternatively" refers to selection of one of two or more alternatives, and is not intended to limit the selection to only those listed alternatives or to only one of the listed alternatives at a time, unless the context clearly indicates otherwise. The term "coupled" as used herein does not require that the components be directly connected to each other. Instead, the term is intended to also include configurations with indirect connections where one or more other components can be included between coupled components. For example, such other components can include amplifiers, attenuators, isolators, directional couplers, redundancy switches, and the like. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples. As used herein, a "set" of elements is intended to mean "one or more" of those elements, except where the set is explicitly required to have more than one or explicitly permitted to be a null set.

Various changes, substitutions, and alterations to the techniques described herein can be made without departing from the technology of the teachings as defined by the appended claims. Moreover, the scope of the disclosure and claims is not limited to the particular aspects of the process, machine, manufacture, composition of matter, means, methods, and actions described above. Processes, machines, manufacture, compositions of matter, means, methods, or actions, presently existing or later to be developed, that perform substantially the same function or achieve substantially the same result as the corresponding aspects described herein can be utilized. Accordingly, the appended claims include within their scope such processes, machines, manufacture, compositions of matter, means, methods, or actions.

What is claimed is:

1. A method for in-time registration of images from temporally separated image acquisition sessions using an imaging apparatus, the method comprising:
    retrieving a stored three-dimensional (3D) image of a portion of a living subject acquired at a prior acquisition time by a first 3D image acquisition system having a 3D sensor acquiring three-dimensional data of the living subject and positioned away from the living subject, the stored 3D image indicating a guide 3D position corresponding to a relative 3D offset between a prior subject location and a prior acquisition location computed as a function of 3D point cloud data of the surface of the living subject acquired by the first 3D image acquisition system at the prior acquisition time;
    measuring a live 3D position of a second 3D image acquisition system having a 3D sensor acquiring 3D data of the living subject and positioned away from the living subject, the live 3D position corresponding to a real-time relative 3D offset between a present subject location and a present acquisition location computed from real-time 3D point cloud data of the surface of the living subject being acquired by the second 3D image acquisition system;
    displaying, in a viewfinder window of the second 3D image acquisition system, a live view being acquired of the portion of the living subject in real time;
    overlaying a 3D guide on the viewfinder window during the displaying of the live view, wherein the 3D guide indicates a real-time positional offset between the live view and the stored 3D image and includes a display of a semi-transparent guide image that includes at least one of a three-dimensional mesh and key feature points, wherein the three-dimensional mesh is implemented as a 3D point cloud generated from the stored 3D image and the key feature points are generated from 3D point cloud data of the stored 3D image, the semi-transparent guide image being graphically positioned on the viewfinder window to be visually correlated with the live view for assisting in real time positioning of the second 3D image acquisition system to achieve in-time registration of the live view with the semi-transparent guide image; and
    acquiring a present 3D image of the live view portion of the living subject.

2. The method of claim 1, further comprising acquiring the present 3D image of the live view portion of the living subject when the live view is in-time registered with the semi-transparent guide image as indicated by the 3D guide.

3. The method of claim 2, wherein the acquiring of the present 3D image of the live view portion of the living subject is in response to receiving a command from a human user when the 3D guide indicates the in-time registration.

4. The method of claim 2, wherein the acquiring of the present 3D image of the live view portion of the living subject comprises acquiring the present 3D image automatically upon detecting the in-time registration within a predefined threshold.

5. The method of claim 1, further deriving a present volumetric measurement of the 3D data of the portion of the living subject based on present three-dimensional image, such that a volumetric change is computed between the present volumetric measurement and a prior volumetric measurement derived from the stored 3D image data of the portion of the living subject acquired at the prior acquisition time by the first 3D image acquisition system.

6. The method of claim 1, wherein:
    the stored three-dimensional image comprises prior three dimensional image data acquired at the prior acquisition time; and
    the acquiring of the live view portion of the living subject comprises acquiring present 3D image data and deriving a present depth measurement of the subject, such that a depth change is computable between the present depth measurement and a prior depth measurement derived from the 3D image acquired at the prior acquisition time.

7. The method of claim 1, wherein the 3D guide further generates a directional indicator that indicates a direction of the real-time 3D offset, such that the direction indicator shows a direction in which to move the second 3D image acquisition system to increase correspondence between the live view and the semi-transparent guide image; and overlays the directional indicator on the viewfinder window.

8. The method of claim 1, wherein overlaying the 3D guide further comprises:
generating a graphical template according to a predefined set of image acquisition criteria used to acquire the stored 3D image; and
overlaying the graphical template on the viewfinder window.

9. The method of claim 1, wherein the 3D guide further includes dynamic feedback indicating a real-time level of correspondence between the live view with the semi-transparent guide image.

10. The method of claim 1, further comprising:
computing a present representative volume of the portion of the living subject from the present 3D image acquired by the second 3D image acquisition system;
computing a prior representative volume of the portion of the living subject from the stored 3D image; and
computing a volumetric difference between the present representative volume and the prior representative volume.

11. The method of claim 1, wherein the first and second three-dimensional image acquisition systems are the same 3D image acquisition system.

12. The method of claim 1, further comprising:
registering the present 3D image and the stored 3D image of the portion of the living subject together subsequent to acquiring the present 3D image of the portion of the living subject.

* * * * *